US012115052B2

(12) United States Patent
Bewick-Sonntag et al.

(10) Patent No.: US 12,115,052 B2
(45) Date of Patent: Oct. 15, 2024

(54) FEMININE HYGIENE PAD WITH ADVANTAGEOUS LATERAL GATHERING FEATURES

(71) Applicant: The Procter & Gamble Company, Cincinnati, OH (US)

(72) Inventors: Christopher Philip Bewick-Sonntag, Cincinnati, OH (US); John David Norcom, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 145 days.

(21) Appl. No.: 17/496,838

(22) Filed: Oct. 8, 2021

(65) Prior Publication Data
US 2023/0111126 A1    Apr. 13, 2023

(51) Int. Cl.
| A61F 13/536 | (2006.01) |
| A61F 13/15 | (2006.01) |
| A61F 13/472 | (2006.01) |
| A61F 13/53 | (2006.01) |
| A61F 13/539 | (2006.01) |

(52) U.S. Cl.
CPC ......... *A61F 13/536* (2013.01); *A61F 13/472* (2013.01); *A61F 2013/15373* (2013.01); *A61F 2013/530343* (2013.01); *A61F 2013/530481* (2013.01); *A61F 2013/53908* (2013.01)

(58) Field of Classification Search
CPC ................ A61F 13/536; A61F 13/472; A61F 2013/15373; A61F 2013/530343; A61F 2013/530481; A61F 2013/53908
See application file for complete search history.

(56) References Cited

U.S. PATENT DOCUMENTS

| 5,795,345 A | 8/1998 | Mizutani et al. |
| 7,942,858 B2 * | 5/2011 | Francoeur ........... A61F 13/4756 604/385.101 |
| 8,993,832 B2 * | 3/2015 | Kuroda ............... A61F 13/4704 604/380 |
| 10,736,795 B2 * | 8/2020 | Bianchi .................... A61F 13/53 |
| 11,141,323 B2 | 10/2021 | Radne et al. |

(Continued)

FOREIGN PATENT DOCUMENTS

WO    2023009191 A1    2/2023

OTHER PUBLICATIONS

16138 PCT Search Report and Written Opinion for PCT/US2022/077452 dated Jan. 24, 2023, 11 pages.

*Primary Examiner* — Leslie A Lopez
*Assistant Examiner* — Timothy L Flynn
(74) *Attorney, Agent, or Firm* — Sarah M. DeCristofaro; William E. Gallagher

(57) ABSTRACT

A feminine hygiene pad having an absorbent structure is disclosed. The absorbent structure may have a plurality of central compression zones disposed in a middle region of the pad, each of the plurality of compression zones being defined by a generally longitudinally-oriented shape having a forward terminus proximate a forward end region of the pad and a rearward terminus proximate a rearward end region of the pad, and an average width between the forward terminus and rearward terminus of 0.5 mm to 2.0 mm, wherein each of the forward terminus and rearward terminus lies no more than 30 percent of the length of the pad, from the lateral axis.

20 Claims, 10 Drawing Sheets

(56) References Cited

U.S. PATENT DOCUMENTS

| | | |
|---|---|---|
| 2008/0021427 A1 | 1/2008 | Iwao |
| 2019/0201251 A1* | 7/2019 | Rosati .................. A61F 13/535 |
| 2021/0169707 A1 | 6/2021 | Suyama |

* cited by examiner

FEMININE HYGIENE PAD WITH ADVANTAGEOUS LATERAL GATHERING FEATURES

BACKGROUND

Conventional feminine hygiene pads, designed to be applied and worn inside underpants in the user/wearer's crotch region, often include absorbent structures substantially constituted by hydrophilic, cellulosic, plant-based fibers such as cotton fibers or wood pulp fibers. The typical absorbent structure includes a layer constituted by a batt or agglomeration of the fibers, which have been deposited via a suitable process, such as airlaying, to a desired basis weight on a formation belt, to form the basic structure. The absorbency of the fibrous structure may be supplemented by including particles or fibers of absorbent gelling material ("AGM"—also known as superabsorbent polymer, or "SAP"), which may be blended with the cellulosic fibers, or combined in a layered configuration with the cellulosic fiber layer.

In many types of pads, a cellulosic fiber-based absorbent structure may be overlaid and thereby combined with an acquisition/distribution layer (often known as a "secondary topsheet," or "STS"), which also may be constituted in whole in part by a batt or agglomeration of fibers. The STS functions to readily accept a relatively sudden or rapid discharge of fluid, and wick and thereby distribute it along the upper/wearer-facing surfaces of the underlying absorbent structure, to maximize efficient use and effectiveness of the absorbent materials therein. In some examples, the STS may be constituted of fibers spun from polymer resin and/or regenerated cellulose (e.g., rayon); in some examples, the STS may include a blend of spun fibers and natural cellulosic fibers.

While such fibrous pad structures are effective at receiving and absorbing discharged fluid, pads including such structures generally do not exhibit a large amount of flexibility in a z-direction, or extensibility or elasticity along x-y directions. In order to include sufficient amounts of absorbent materials to provide the user/wearer with protection against leakage of fluid (which can soil underwear and outer clothing, etc.) for a reasonably convenient duration of time, and to provide effective body coverage proximate the vaginal opening, the pad must be sized with a minimum width and surface area, and include minimum amounts of the absorbent materials, disposed in appropriate locations and at appropriate basis weights within the pad relative its intended positioning with respect to the user/wearer's body. The pad also is forced to conform to the wearer's body contours, and shift along varying directions and to varying extents, to accommodate the wearer's body movements. As a consequence of these constraints and usage demands, the conventional pad is forced to buckle, gather or bunch to varying extents along a lateral direction, to fit and move within the physical space within the underpants in the user/wearer's crotch region, where it is required to serve its function.

Current pads having the structure and components described above often do not laterally buckle or gather in a predictable or orderly manner. As a result, such a pad may buckle or even bunch in a manner that causes the user/wearer discomfort. Further, uncontrolled shifting, buckling and bunching may result in a mis-location of absorbent components and a loss of effective placement and contact with the wearer's body, increasing a likelihood of fluid leakage.

Accordingly, any features that provide for more controlled lateral gathering in feminine hygiene pads of conventional composition and structure, in a manner that helps maintain and/or improve user/wearer comfort and body coverage, would provide benefits to users/wearers, and provide competitive advantage to the manufacturer and/or seller thereof.

DESCRIPTION OF THE FIGURES

In FIGS. 1-9, the x-y-z direction indicator arrows indicate lateral (x), longitudinal (y) and caliper/thickness (z) directions along the depicted pad or depicted components thereof. In FIG. 10, the x-z indicator arrows indicate the cross-machine direction (x), and pad caliper/thickness direction (z), respectively.

DETAILED DESCRIPTION OF EXAMPLES

Definitions

Figure 1:
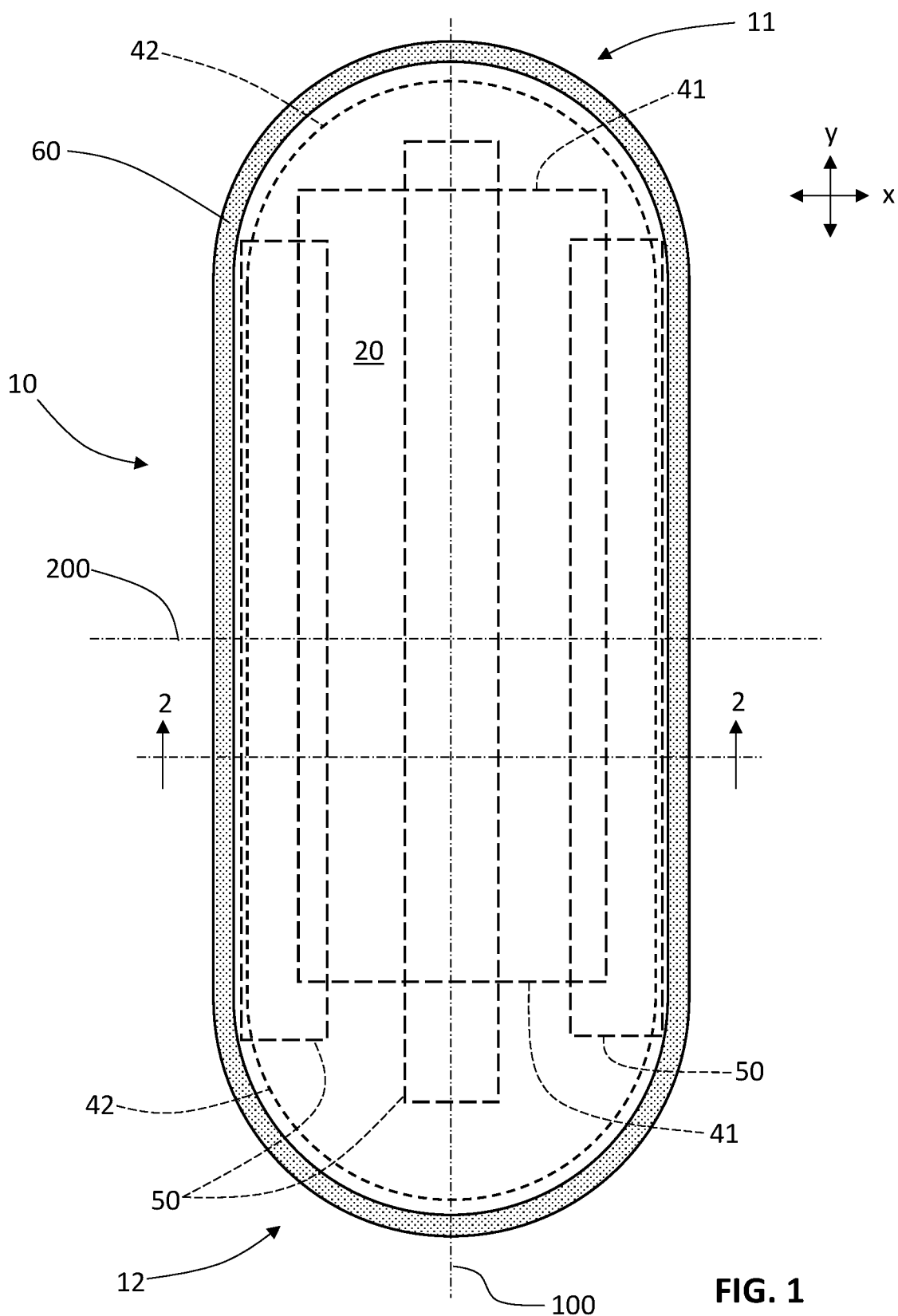
FIG. 1 is a schematic plan view of an example of a feminine hygiene pad.

A "compression zone" is an identifiable region of a feminine hygiene pad or any layer component or combination of layer components thereof in which the material(s) thereof bear evidence of having been compressed in a z-direction.

A "feminine hygiene pad" is an assembly of components including absorbent materials, configured to be placed and worn directly facing the body of a human female, in a position proximate the vagina.

"Lateral"—with respect to a feminine hygiene pad or a component thereof, refers to a direction parallel to a horizontal line tangent to the front surfaces of the upper portions of wearer's legs proximate the torso, when the pad is being worn normally and the wearer has assumed an even, square, normal standing position. A "width" dimension of any component or feature of a feminine hygiene pad is measured along the lateral direction. When the feminine hygiene pad or component thereof is laid out flat on a horizontal surface, the "lateral" direction corresponds with the lateral direction relative the structure when it is worn, as defined above. With respect to a feminine hygiene pad that is opened and laid out flat on a horizontal planar surface, "lateral" refers to a direction perpendicular to the longitudinal direction and parallel to the horizontal planar surface.

The "lateral axis" of a feminine hygiene pad or component thereof is a lateral line lying in an x-y plane and equally dividing the length of the pad or the component when it is laid out flat on a horizontal surface. A lateral axis is perpendicular to a longitudinal axis.

"Longitudinal"—with respect to a feminine hygiene pad or a component thereof, refers to a direction perpendicular to the lateral direction. A "length" dimension of any component or feature of a feminine hygiene pad is measured along the longitudinal direction from its forward extent to its rearward extent. When a feminine hygiene pad or component thereof is laid out flat on a horizontal surface, the "longitudinal" direction is perpendicular to the lateral direction relative the pad when it is worn, as defined above.

The "longitudinal axis" of a feminine hygiene pad or component thereof is a longitudinal line lying in an x-y plane and equally dividing the width of the pad or component, when the pad is laid out flat on a horizontal surface. A longitudinal axis is perpendicular to a lateral axis.

"x-y plane," with reference to a feminine hygiene pad or component thereof when laid out flat on a horizontal surface, means any horizontal plane occupied by the horizontal surface or any layer of the pad or component.

"z-direction," with reference to a feminine hygiene pad or component thereof when laid out flat on a horizontal surface, is a direction orthogonal to the x-y plane.

With respect to a feminine hygiene pad or component thereof, the terms "front," "rear," "forward" and "rearward" and similar relative locational terms relate to features or regions of the pad corresponding to the position they would occupy as ordinarily worn by a user/wearer, corresponding with the front (anterior) and rear (posterior) of the user/wearer's body when standing.

With respect to a feminine hygiene pad, "wearer-facing" is a relative locational term referring to a feature of a component or structure of the pad that when in use that lies closer to the wearer than another feature of the component or structure. For example, a topsheet has a wearer-facing surface that lies closer to the wearer than the opposite, outward-facing surface of the topsheet.

With respect to a feminine hygiene pad, "outward-facing" is a relative locational term referring to a feature of a component or structure of the pad that when in use that lies farther from the wearer than another feature of the component or structure. For example, a topsheet has an outward-facing surface that lies farther from the wearer than the opposite, wearer-facing surface of the topsheet.

The terms "top," "bottom," "upper," "lower," "over," "under," "beneath," "superadjacent," "subjacent," and similar terms relating to relative vertical positioning, when used herein to refer to layers, components or other features of a feminine hygiene pad, are relative a z-direction and are to be interpreted with respect to the pad as it would appear when laid out flat on a horizontal surface, with its wearer-facing surface oriented upward and outward-facing surface oriented downward.

Description

General

Figure 2:
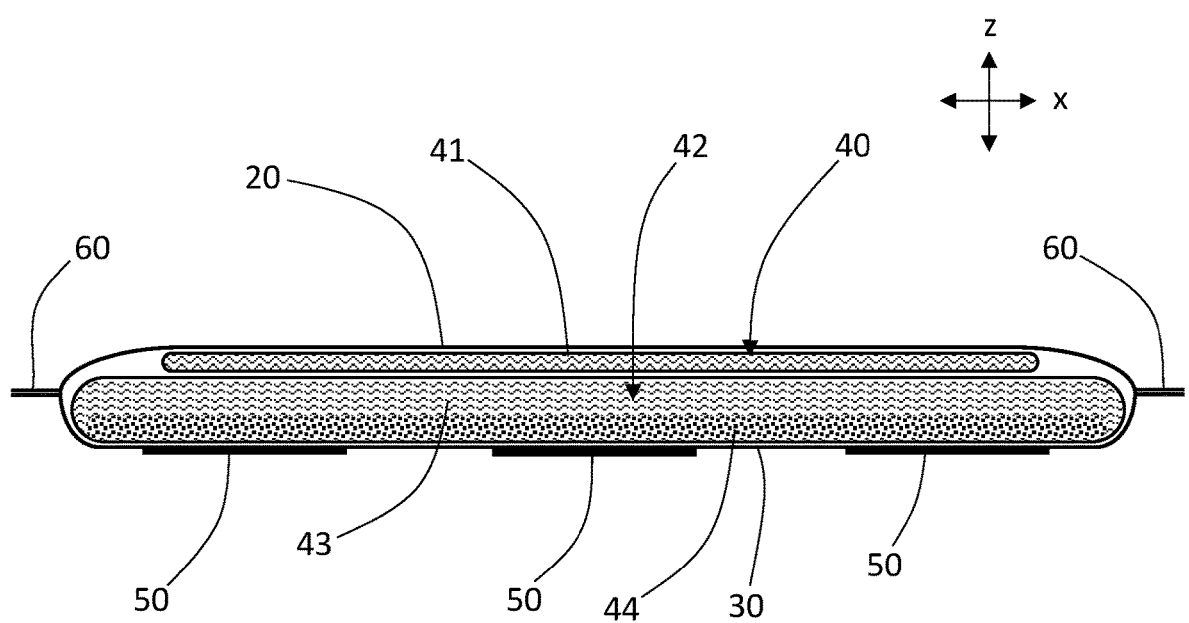
FIG. 2 is a schematic lateral cross section of the feminine hygiene pad shown in FIG. 1, taken along line 2-2 shown in FIG. 1.

Referring to FIGS. 1 and 2, a feminine hygiene pad 10 will have a forward end 11, a rearward end 12, and may include a liquid permeable topsheet 20, a liquid impermeable backsheet 30 and an absorbent core 40 disposed between the topsheet and the backsheet. The topsheet 20 and backsheet 30 may be bonded by any suitable mechanism at a peripheral seam 60, to form a closed enveloping structure about and containing the components of the absorbent core 40. The absorbent core 40 may include an absorbent structure 42. In some examples the absorbent core may include an acquisition/distribution layer or secondary topsheet ("STS") 41. The pad 10 may be imparted with any suitable shape, generally elongate in the x-y plane and having a length greater than its width, such as an elongate stadium shape as shown, or any other suitable shape including a rectangle shape or trapezoid shape (which may be rounded), oval shape, elliptical shape, ellipsoid shape, ovoid shape, peanut shape, hourglass shape, etc., found in feminine hygiene pads as have been manufactured and known in the art.

Topsheet

Topsheet 20 may be formed of any suitable nonwoven web material. Referring back to the figures, the topsheet 20 is positioned adjacent a wearer-facing surface of the absorbent structure 40 and may be joined thereto and to the backsheet 30 by any suitable attachment or bonding method. The topsheet 20 and the backsheet 30 may be joined directly to each other in the peripheral regions outside the perimeter of the absorbent structure and may be indirectly joined by directly joining them respectively to wearer-facing and outward-facing surfaces of the absorbent structure or additional optional layers included with the pad.

The pad 10 may have any known or otherwise effective topsheet 20, such as one which is compliant, soft feeling, and non-irritating to the wearer's skin. A suitable topsheet material will include a liquid pervious material that is comfortable when in contact with the wearer's skin and permits discharged menstrual fluid to rapidly penetrate through it. A suitable topsheet may be made of any of various materials such as woven or knitted materials, nonwoven web materials, or apertured films.

Nonlimiting examples of nonwoven web materials that may be suitable for use to form the topsheet 20 include fibrous materials made from natural fibers, modified natural fibers, synthetic fibers, or combinations thereof. Some suitable examples are described in U.S. Pat. Nos. 4,950,264; 4,988,344; 4,988,345; 3,978,185; 7,785,690; 7,838,099; 5,792,404; and 5,665,452.

In some examples, the topsheet 20 may include tufts as described in U.S. Pat. Nos. 8,728,049; 7,553,532; 7,172,801; 8,440,286; 7,648,752; and 7,410,683. The topsheet 20 may have a pattern of discrete hair-like fibrils as described in U.S. Pat. No. 7,655,176 or U.S. Pat. No. 7,402,723. Additional examples of suitable topsheet materials include those described in U.S. Pat. Nos. 8,614,365; 8,704,036; 6,025,535 and US 2015/041640. Another suitable topsheet may be formed from a three-dimensional substrate as detailed in US 2017/0258647. The topsheet may have one or more layers, as described in US 2016/0167334; US 2016/0166443; and US 2017/0258651.

In some examples a topsheet 20 may be formed of a nonwoven web material of a spunbond web including single-component continuous fibers, or alternatively, bi-component or multi-component fibers, or a blend of single-component fibers spun of differing polymer resins, or any combination thereof. In some examples a web may be formed in a co-forming process in which plant-based fibers of finite lengths are physically blended or mixed with streams of spun fibers of longer but indefinite lengths, spun from polymeric resin, and laid down on a forming belt to form a web as described in, for example, U.S. Pat. Nos. 8,017,534; 4,100,324; US 2003/0200991; U.S. Pat. No. 5,508,102; US 2003/0211802; EP 0 333 228; WO 2009/10938; US 2017/0000695; US 2017/0002486; U.S. Pat. No. 9,944,047; 2017/0022643 and US 2018/0002848.

In order to ensure that fluid contacting the top (wearer-facing) surface of a topsheet will move suitably rapidly via capillary action in a z-direction to the bottom (outward-facing) surface of the topsheet where it can be drawn into the absorbent structure, it may be important to ensure that the nonwoven web material forming the topsheet has an appropriate weight/volume density, reflecting suitable presence of interstitial passageways (sometimes known as "pores") among and between the constituent fibers, through which fluid may move within the nonwoven material. In some circumstances a nonwoven material with fibers that are consolidated too densely will have insufficient numbers and/or volumes and/or sizes of pores, and the nonwoven will obstruct rather than facilitate rapid downward z-direction fluid movement. On the other hand, a nonwoven with fibers that are too large and/or not consolidated enough to provide a certain level of opacity (for purposes of concealing absorbed fluid in the layers beneath) and a substantial appearance may be negatively perceived by users.

In combination with adjustment of pore size, volume and number via selection of appropriate fiber size, basis weight, and extent of consolidation, the manufacturer may wish to select fiber constituents for having particular surface chemistry(ies), e.g., fibers with hydrophobic surfaces, hydrophilic surfaces, or a blend of differing fibers and/or z-direction stratification of gradient thereof. Fibers having hydrophilic surfaces will tend to attract and move aqueous components of menstrual fluid therealong in a manner conducive to wicking and rapid fluid acquisition following discharge. At the same time, however, a predominance of hydrophilic fibers surfaces within the topsheet may increase a tendency of the topsheet to reacquire fluid from absorbent components beneath (rewet), which can cause an undesirable wet feel for the user. On the other hand, fibers having hydrophobic surfaces will tend to repel aqueous components of menstrual fluid and/or resist movement of fluid along their surfaces, thereby tending to resist wicking—but also to resist rewetting. The manufacturer may wish to seek an appropriate balance in selecting constituent fibers having hydrophilic surfaces, fibers having hydrophobic surfaces, or a blend and/or z-direction stratification thereof, in combination with fiber size, fiber consolidation level, and resulting topsheet pore size, volume and number, for any particular product design. Selection of the underlying absorbent components, e.g., STS 41 and absorbent structure 42, will also impact these choices. Generally, it may be desired that the materials constituting the STS 41 and/or absorbent structure 42 have a greater attraction for the fluid than the topsheet, so as to reduce the likelihood that the topsheet will reacquire fluid from these underlying layer components.

The caliper of the topsheet material may be controlled, to balance competing needs for opacity and loft (which call for a higher caliper) vs. a limitation on the z-direction distance that discharged fluid must travel through the topsheet from the wearer-facing surface to the outward-facing surface, to reach the absorbent core components below. Thus, it may be desired that the manufacture of the topsheet material be controlled to produce a topsheet material having a caliper of 0.20 mm to 1.0 mm, more preferably 0.25 mm to 0.80 mm, and even more preferably 0.30 mm to 0.60 mm. For purposes herein, caliper is measured using the caliper measurement method set forth below.

Absorbent Core

An absorbent core 40 may include an STS 41 and an absorbent structure 42.

Secondary Topsheet (STS)

The STS may be included in some circumstances to enable the absorbent core to readily receive a sudden discharge of fluid, and after receipt, to wick it along x- and y-directions to distribute it across the underlying absorbent core structure.

If included, an STS 41 may be a nonwoven fibrous structure which may include cellulosic fibers, non-cellulosic fibers (e.g., fibers spun from polymer resin(s)), or a blend thereof. To accommodate the folding and lateral gathering of the absorbent structure 42, and of the pad 10, as described herein, it may be preferred that STS 41 be formed of a material that is relatively pliable (i.e., has relatively low bending stiffness).

STS 41 may be a nonwoven material formed of integrated, carded fibers materials. A wide variety of configurations for an STS may be manufactured. However, it may be deemed important that the STS have sufficient openness to allow for quick acquisition of menstrual fluid, yet also be able to lock away fluid, to reduce the likelihood of rewetting the topsheet. An STS may be manufactured from a plurality of carded precursor batts. The carded batts may be different from one another. For example, one of the carded batts may comprise a different fiber blend than the others. In some examples, where a first carded batt is disposed in a position proximate a wearer-facing surface of the finished pad, the fiber selection for such first carded batt may be such that it imparts relatively greater openness as compared with than carded batt(s) disposed therebeneath. A second carded batt subjacent the first carded batt may be included and similarly composed. In some examples, alternatively or in contrast, a second or third carded batt subjacent a first or second carded batt may have a composition selected to impart it with relatively greater wicking capability, and the ability to draw or collect fluid from within the void spaces of the first and/or second carded batts webs, and effectively wick and distribute the fluid to and across an underlying/subjacent absorbent structure 42.

The first, second, and if included, third carded precursor batts may be integrated to form a cohesive web structure via a known z-direction fiber integration process, for example, needlepunching or hydroentanglement/spunlacing.

After the carded precursor batt(s) are integrated, they form a cohesive web structure and cannot be readily separated. However, each carded batt may form an identifiable stratum in the STS 41. Each stratum can maintain its unique properties for at least a portion of the stratum along the z-direction, even after being integrated. The STS provides capillary suction to draw fluid through the topsheet 20, which, depending upon its configuration and composition, may tend to compete with the STS to retain fluid in low volume/velocity flow conditions. The STS also, however, can receive and diffuse energy from a "gush" (relatively rapid discharge) of fluid by providing void space, wicking and distribution functions to receive and distribute fluid and efficiently utilize the absorbent structure, as well as provide interim storage capability until the absorbent structure can accept and absorb the fluid.

For purposes herein, an STS 41 may be provided with a basis weight of up to 75 grams per square meter (gsm); or a basis weight of up to 70 gsm; or a basis weight in the range of about 40 gsm to about 75 gsm; or in the range of about 50 gsm to about 70 gsm; or in the range of about 55 gsm to about 65 gsm, including any values within these ranges and any ranges created thereby. In another specific example, the STS 41 may have a basis weight of between 40 gsm to 60 gsm.

As a benefit of fiber integration, a cohesive STS 41 structure may be manufactured that does not require adhesives or latex binders for stability and structural integrity sufficient for manufacturing purposes and for shape retention when wetted. Additionally, the carded staple-fiber nonwoven of the STSs contemplated herein can be manufactured from an assortment of suitable fiber types that produce the desired performance characteristics which is discussed below.

The types of fibers included to constitute the STS may be selected for their contributions to functionality within the STS. For example, absorbent fibers such as fibers of cotton and/or regenerated cellulose (e.g., rayon, viscose) may be included to draw and wick fluid, and provide temporary storage. Stiffening fibers spun from polymer resin(s) may be included, which may be bonded together via heat treatment (e.g., air through bonding) thereby providing a springy, resilient feel and structural integrity to the STS. Resilient fibers, also spun from polymer resin(s), may be included to further impart the STS with the ability to retain its shape when wetted, to recover its shape and caliper following application of compressive forces on the STS, and to provide and/or enhance a resilient, cushiony feel to the STS.

To enhance the stabilizing effect of the integration, crimped or curled fibers may be included. Fibers may be mechanically crimped via, e.g., passage through a pair of rollers with intermeshing teeth. Alternatively, or in addition, crimped or curled fibers may be spun from bicomponent configurations that cause them to crimp or curl as they cool and solidify following exit of the polymer components from suitably configured spinnerets. Absorbent fibers also may be mechanically crimped, and/or, may be provided with a chemically-induced crimp.

In some examples the STS 41 may be constituted of about 15 percent to about 60 percent by weight, or about 20 percent to about 50 percent by weight, about 25 percent to about 40 percent by weight, specifically including any values within these ranges and any ranges created thereby of absorbent fibers. In one specific example, the STS may have about 30 percent by weight of absorbent fibers.

In some examples the STS 41 may be constituted of about 20 percent to about 70 percent, about 30 percent to about 60 percent, about 35 percent to about 50 percent by weight of resilient fibers, specifically reciting all values within these ranges and any ranges created thereby. In one specific example, an STS 41 may have about 40 percent by weight resilient fibers.

In some examples, the STS 41 may be constituted of about 15 percent to about 60 percent, about 20 percent to about 50 percent, or about 25 percent to about 40 percent of stiffening fibers, specifically reciting all values within these ranges and any ranges created thereby. In one specific example, an STS 41 may have about 30 percent by weight stiffening fibers.

The weight fraction of stiffening fibers included may be greater than or equal to the weight fraction of resilient fibers included. The weight fraction of absorbent fibers included may be less than the weight fractions of resilient fibers and/or stiffening fibers included. In general, a higher weight fraction of absorbent fibers is considered to be beneficial for purposes of rapid absorption of fluid; however, given the proximity of the STS to the topsheet, it is beneficial for the absorbent structure 41 to draw fluid from the STS. Accordingly, where there is a relatively greater weight fraction of absorbent fibers in the STS, a larger absorbent structure may be required is required to draw fluid from the absorbent fibers. This may involve to higher material costs. Accordingly, it may be desired that a weight ratio of absorbent fibers to stiffening fibers in the STS be less than 1:1, less than 0.6:1, or less than 0.5:1, specifically reciting all values within these ranges and any ranges created thereby. Similarly, it may be desired that a weight ratio of absorbent fibers to resilient fibers in the STS be less than 1:1, less than 0.8:1, or less than 0.7:1, specifically reciting all values within these ranges and any ranges created thereby.

Any suitable type(s) of absorbent fibers may be selected. Some conventional and suitable absorbent fibers may include cotton, regenerated cellulose (e.g., rayon, viscose) or combinations thereof. In some examples, the STS may include viscose fibers.

The absorbent fibers included may be staple-length fibers. The average staple length of the absorbent fibers may be selected to be in the range of about 20 mm to about 100 mm, or about 30 mm to about 50 mm or about 35 mm to about 45 mm, specifically reciting all values within these ranges and any ranges created thereby.

Absorbent fibers of any suitable average linear density may be selected. For example, the average absorbent fiber linear densities may be about 1 dtex to about 7 dtex, about 1.4 dtex to about 6 dtex, or about 1.7 dtex to about 5 dtex, specifically reciting all values within these ranges and any ranges created thereby. In one specific example, the absorbent fiber may have an average linear density of about 1.7 dtex.

Each stratum may include fibers of the same transverse cross section shape, or have fibers of respectively differing transverse cross section shapes. (Herein, the "shape" of a fiber refers to the shape of the outer profile of its cross section, along a plane transverse to its longest dimension.)

The absorbent fibers of the STS may imparted with any suitable shape. Some examples of shapes include trilobal, "H," "Y," "X," "T," or round. Further, the absorbent fibers may be solid, hollow or multi-hollow. Other examples of suitable multi-lobed, absorbent fibers for utilization in the carded staple-fiber nonwovens described herein are described in U.S. Pat. Nos. 6,333,108, 5,634,914, and 5,458,835. Fibers having a multilobal cross section shape, e.g., a trilobal shape, can impart to the STS enhanced wicking performance and stain-concealing properties, i.e., increased the opacity, as compared with fibers of simpler cross section shapes such as round shapes. One example of a suitable trilobal rayon fiber is available from Kelheim Fibres GmbH (Kelheim, Germany) and sold under the trade name Galaxy.

Each stratum may include absorbent fibers of the same shape, or have absorbent fibers of respectively differing shapes.

As noted above, in addition to absorbent fibers, the STS may also include stiffening fibers. Stiffening fibers may be included to help provide structural integrity to the STS. The stiffening fibers can help increase structural integrity of the STS in both a machine direction (MD) and in a cross-machine direction (CD), which can facilitate web manipulation during processing of the STS for incorporation into a pad. With that in mind, the constituent material of the stiffening fibers, the weight fraction of the stiffening fibers, and heat of processing should be carefully selected. The heat stiffening process is discussed below.

Stiffening fibers of any suitable average linear density may be selected. For example, the stiffening fiber average linear density may range from about 1.7 dtex to about 12 dtex, from about 4 dtex to about 10 dtex, or from about 5 dtex to about 7 dtex, specifically reciting all values within these ranges and any ranges created thereby. In one specific example, the stiffening fibers may comprise linear density of about 5.8 dtex.

Stiffening fibers of any suitable composition may be selected. Some examples of suitable stiffening fibers include bi-component fibers comprising polyethylene (PE) and polyethylene terephthalate (PET) components or polyethylene terephthalate and co-polyethylene terephthalate components. The components of the bi-component fiber may be arranged in a sheath-core configuration, a side-by-side configuration, an eccentric sheath-core configuration, a trilobal arrangement, or any other desired configuration. In one example, the stiffening fibers may include bi-component fibers having PE/PET components arranged in a concentric, sheath-core configuration, wherein the polyethylene component forms the sheath.

While other materials may be useful in creating a resilient structure, it is believed that the stiffness of a PET core component in a sheath-core fiber configuration is useful for imparting resilience to the STS. In synergistic combination, a PE sheath component, having a lower melting temperature than the PET core component, may be utilized to provide inter-fiber melt/fusion bonding, effected via heat treatment of the precursor batt. This can help provide tensile strength to the web in both the MD and CD. Such inter-fiber bonds may serve to reduce fiber-to-fiber sliding, and thereby further contribute to imparting shape stability and resiliency to the material even when it is wetted.

Where a relatively higher weight fraction of stiffening fibers is included, more connections within the structure may be created via heat treatment. However, too many connection points can impart greater stiffness to the STS than may be desirable. For this reason, the selecting the weight fraction of the stiffening fibers may involve prioritizing and balancing competing needs for stiffness and softness in the STS.

In the heat stiffening process, selection of a suitable treatment temperature will depend upon the respective softening and melting temperatures of the fiber constituents and components thereof. It may be preferred generally, that a heat treatment temperature be a low as possible but sufficient to effect melt fusion between stiffening fiber components such as PE, without causing melting of other components. The precursor batt may be heated by any process suitable for evenly/uniformly heating the STS prescursor to the desired temperature, for example, an air-through process.

As noted above, the STS may additionally include resilient fibers. The resilient fibers can help the STS maintain permeability and compression recovery. Fibers of any suitable average size or linear density may be utilized. For example, the resilient fibers may have an average linear density of about 1 dtex to about 12 dtex, about 2 dtex to about 7 dtex, or about 3 dtex to about 5 dtex, specifically reciting all values within these ranges and any ranges created thereby. In one example, the resilient fibers may have an average linear density of about 4.4 dtex. In another example, the STS may comprise resilient fibers having varying cross sections, e.g. round and hollow spiral, and/or may comprise resilient fibers having varying sizes.

The resilient fibers may be spun from any suitable thermoplastic resin, such as polypropylene (PP), polyethylene terephthalate (PET), or other suitable thermoplastics known in the art. The average staple length of the resilient fibers may be selected to be in the range of about 20 mm to about 100 mm, or about 30 mm to about 50 mm or about 35 mm to about 45 mm. The resilient fibers may have any suitable structure or shape. For example, the resilient fibers may be round or have other shapes, such as spiral, scalloped oval, trilobal, scalloped ribbon, and so forth. Further, the resilient fibers may be solid, hollow or multi-hollow. The resilient fibers may be solid and round in shape. In other suitable examples, resilient fibers may include polyester/co-extruded polyester fibers. Other suitable examples of resilient fibers may include bi-component fibers such as polyethylene/polypropylene, polyethylene/polyethylene terephthalate, polypropylene/polyethylene terephthalate bicomponent fibers. These bi-component fibers may have a sheath/core configuration. The bi-component fibers may provide a cost-effective way to increase basis weight of the material while additionally enabling optimization of the pore size distribution.

The resilient fibers may also be polyethylene terephthalate (PET) fibers, or other suitable non-cellulosic fibers known in the art. PET fibers may be imparted with any suitable structure or shape. For example, the PET fibers may be round or have other shapes, such as spiral, scalloped oval, trilobal, scalloped ribbon, hollow spiral, and so forth. The PET fibers may be solid, hollow or multi-hollow. In one particular example, PET fibers may be hollow in cross section and have a curl or spiral configuration along their lengths. Optionally, the resilient fibers may be spiral-crimped or flat-crimped. The resilient fibers may have an average crimp count of about 4 to about 12 crimps per inch (cpi), or about 4 to about 8 cpi, or about 5 to about 7 cpi, or about 9 to about 10 cpi. Particular non-limiting examples of resilient fibers may be obtained from Wellman, Inc. (Ireland) under the trade designations H1311 and T5974. Other examples of suitable resilient fibers are disclosed in U.S. Pat. No. 7,767,598.

The stiffening fibers and resilient fibers should be carefully selected. For example, while the constituent polymers forming the stiffening fibers and the resilient fibers may have similarities, resilient fiber composition should be selected such that their constituents' melting temperature(s) is/are higher than that of the bondable components of the stiffening fibers. Otherwise, during heat treatment, resilient fibers could bond to stiffening fibers and vice versa, and thereby an overly rigid structure. To avoid this risk where the stiffening fibers include bicomponent fibers, e.g., core-sheath configuration fibers with a sheath component of relatively lower melting temperature at which fusion bonding will occur, the resilient fibers may comprise the constituent chemistry of only the core, which may be a polymer having a relatively higher melting temperature.

A number of particular examples of suitable STS compositions and structures, as well as combinations thereof with suitable topsheet compositions and structures, are further described in U.S. application Ser. Nos. 16/831,862; 16/831,854; 16/832,270; 16/831,865; 16/831,868; 16/831,870; and Ser. No. 16/831,879; and U.S. Provisional Apps. Ser. Nos. 63/086,610 and 63/086,701. Additional suitable examples are described in U.S. Pat. No. 9,504,613; WO 2012/040315; and US 2019/0021917.

Absorbent Structure

In some examples the absorbent structure 42 may include a formed batt or formed agglomeration including cellulosic fibers 43. In some examples the absorbent structure 42 may include a distribution of absorbent gelling material ("AGM"—also known as superabsorbent polymer ("SAP")) particles or fibers 44. The AGM particles or fibers may be blended and distributed substantially uniformly throughout the absorbent structure and among the cellulosic fibers 43, or may be stratified so as to have a greater weight/volume concentration in lower regions of the absorbent structure 42. In some examples a distinct lower layer of the absorbent structure 42 may include AGM particles or fibers, while a distinct upper layer of the absorbent structure 42 may include only fibers. In some examples the absorbent structure 42 may include a layer formed of or including an open-celled foam, such as a polyurethane foam or HIPE foam.

The configuration and construction of the absorbent structure 42 may vary (e.g., the absorbent structure 42 may have varying caliper zones, a hydrophilic z-direction gradient or stratification, a z-direction gradient or stratification of AGM location or distribution, average density and average basis weight variations, and any combinations of these. Further, the size and absorbent capacity of the absorbent structure 42 may be varied to accommodate a variety of wearer needs and/or varied conditions of wear/use, e.g., nighttime/extended or daytime/active/shorter duration. However, the total absorbent capacity of the absorbent structure 42 should be compatible with the design loading and the intended use of the pad.

In some forms, the absorbent structure 42 may include a plurality of multi-functional layers. For example, the absorbent structure 42 may include a core wrap (not shown) useful for enveloping distinct layers. The core wrap may be formed by two nonwoven materials, substrates, laminates, films, or other materials. In a form, the core wrap may only comprise a single material, substrate, laminate, or other material wrapped at least partially around itself.

The absorbent structure 42 of the present disclosure may comprise one or more adhesives, for example, to help immobilize the AGM materials or other absorbent materials within layers thereof.

Absorbent structures comprising relatively high amounts of SAP with various absorbent structure/core designs are disclosed in U.S. Pat. No. 5,599,335; EP 1,447,066; WO 95/11652; US 2008/0312622A1 to Hundorf et al.; and WO 2012/052172. These may be instructive for configuring superabsorbent layers.

Additions to the absorbent structure of the present disclosure are envisioned. In particular, potential additions to the current multi-laminate absorbent structure are described in U.S. Pat. Nos. 4,610,678; 4,673,402; 4,888,231; and 4,834,735. The absorbent structure may further comprise additional layers that mimic the dual core system containing an acquisition/distribution structure of chemically stiffened fibers positioned over an absorbent structure as detailed in U.S. Pat. No. 5,234,423; and in U.S. Pat. No. 5,147,345.

These are useful to the extent they do not negate or conflict with the effects of the below described laminates of the absorbent structure of the present invention.

Some examples of suitable absorbent structures 40 that can be used in the absorbent article of the present disclosure are described in US 2018/0098893 and US 2018/0098891. Further examples of possible suitable configurations are described and depicted in U.S. application Ser. Nos. 16/831,851 and 14/729,107; and in U.S. Pat. No. 10,322,039.

Backsheet

The backsheet 30 may be positioned beneath or subjacent an outward-facing surface of the absorbent structure 42 and may be joined thereto by any suitable attachment methods. For example, the backsheet 30 may be secured to the absorbent structure 42 by a uniform continuous layer of adhesive, a patterned layer of adhesive, or an array of separate lines, spirals, or spots of adhesive. Alternatively, the attachment method may include heat bonds, pressure bonds, ultrasonic bonds, dynamic mechanical bonds, or any other suitable attachment mechanisms or combinations thereof. In other examples, it is contemplated that the absorbent structure 42 is not joined directly to the backsheet 30.

The backsheet 30 may be impermeable or substantially impermeable by aqueous liquids (e.g., urine, menstrual fluid) and may be manufactured from a thin plastic film, although other flexible liquid impermeable materials may also be used. As used herein, the term "flexible" refers to materials which are compliant and will readily conform to the general shape and contours of the human body. The backsheet 30 may prevent, or at least substantially inhibit, fluids absorbed and contained within the absorbent structure 40 from escaping and reaching articles of the wearer's clothing which may contact the pad 10, such as underpants and outer clothing. However, in some instances, the backsheet 30 may be made and/or adapted to permit vapor to escape from the absorbent structure 40 (i.e., the backsheet is made to be breathable), while in other instances the backsheet 30 may be made so as not to permit vapors to escape (i.e., it is made to be non-breathable). Thus, the backsheet 30 may comprise a polymeric film such as thermoplastic films of polyethylene or polypropylene. A suitable material for the backsheet 30 is a thermoplastic film having a thickness of from about 0.012 mm (0.5 mil) to about 0.051 mm (2.0 mils), for example. Any suitable backsheet known in the art may be utilized with the present invention.

Some suitable examples of materials suitable for forming a backsheet are described in U.S. Pat. Nos. 5,885,265; 4,342,314; and 4,463,045. Suitable single layer breathable backsheets for use herein include those described for example in GB A 2184 389; GB A 2184 390; GB A 2184 391; U.S. Pat. Nos. 4,591,523, 3,989,867, 3,156,242; WO 97/24097; U.S. Pat. Nos. 6,623,464; 6,664,439 and 6,436,508.

The backsheet 30 may have two layers: a first layer comprising a vapor permeable aperture-formed film layer and a second layer comprising a breathable microporous film layer, as described in U.S. Pat. No. 6,462,251. Other suitable examples of dual or multi-layer breathable backsheets for use herein include those described in U.S. Pat. Nos. 3,881,489, 4,341,216, 4,713,068, 4,818,600; EP 203 821. EP 710 471; EP 710 472, and EP 0 793 952.

Other Features

In some examples, pad 10 may be provided with adhesive deposits 50, to provide a mechanism for the user to adhere the pad to the inside of her underpants in the crotch region thereof. When pad 10 is packaged for shipping, handling and storage prior to use, adhesive deposits 50 may be covered by one or more sheets of release film or paper (not shown) that covers/shields the adhesive deposits 50 from contact with other surfaces until the user is ready to remove the release film or paper and place the pad in her underpants for wear/use.

In some examples, pad 10 may include opposing wing portions (not shown) at each side, extending laterally beyond longitudinal edges of the absorbent portions of the pad by a comparatively greater width dimension than that of the forward and rearward portions of the pad. Wings are currently commonly provided with feminine hygiene pads. As provided, they typically have deposits of adhesive applied to their outward-facing surfaces (surface are outward-facing prior to placement of the pad within the user's underwear and application of the wings). The wing portions may also include deposits of adhesive as described above, which enable the user to wrap the wing portions through the leg openings of the underpants and around the inside edges thereof, and adhere the wing portions to the outward-facing surface/underside of the underpants in the crotch region, providing supplemental holding support for the pad and helping guard the underpants proximate the leg edges thereof against soiling.

Compression Zones

If a pad were to be precisely shaped to accommodate a particular wearer's body features, its absorbent structure might be imparted with an hourglass-like or "waisted" profile with deep concave cuts along the longitudinal sides, narrowing and converging at the portion of the pad intended to be disposed directly between the wearer's legs. While such a deeply waisted profile might better fit within the crotch region of some wearers as compared with another pad not having such a profile, it would reduce body coverage and also reduce the amount of absorbent material that might be disposed proximate to the vaginal opening, where it is needed most for intercepting, accepting and absorbing discharged fluid. Further, manufacture of pads having a waisted profile typically is less efficient and/or can generate greater quantities of cutoff/scrap material. For these reasons, many conventional pads having cellulosic fiber-based absorbent structures are configured and manufactured to have longitudinal sides with profiles that are predominantly or entirely straight.

The components and materials of a conventional feminine hygiene pad with a cellulosic fiber-based absorbent structure typically do not provide for a pad that has a significant degree of z-direction flexibility, or x-y direction extensibility, elasticity or conformability. When such a pad is placed within underpants for use/wear, it may not easily and readily conform in a controlled manner to the space within the user's underpants and between the wearer's legs, so as to provide for effective contact with the wearer's body such as to minimize chances for leakage of discharged fluid. The pad also may not flex easily with the wearer's body movements. As a consequence, the pad may buckle and bunch in an uncontrolled manner and may become dislocated from its intended placement location and/or most effective position, and may become a source of discomfort for the wearer and/or cause a bulky, disorderly, indiscreet appearance through outer clothing.

Ideally the pad will laterally gather to some extent at particular locations, to fit within the space between the wearer's legs, at its intended position for use. As noted, such gathering in many circumstances and pad configurations may be irregular and uncontrolled. It has been discovered, however, that a pad having a combination of absorbent components including cellulosic fibers as described herein may be mechanically processed to impart features that control and improve the manner in which the pad gathers in a lateral direction when placed by a user/wearer within her underpants for use.

Figure 3:
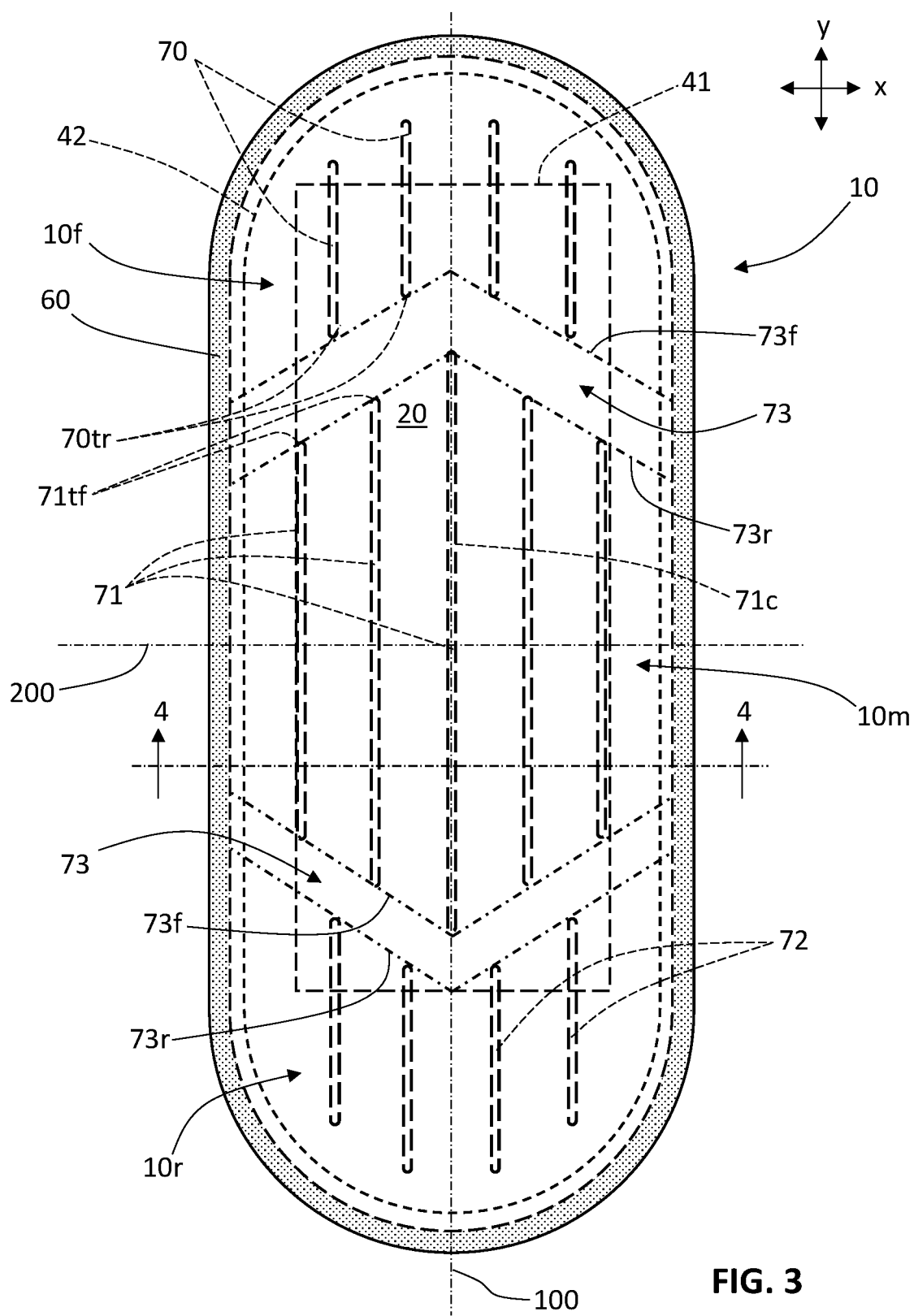
FIG. 3 is a schematic plan view of an example of a feminine hygiene pad having a configuration of compression zones.
Figure 4:
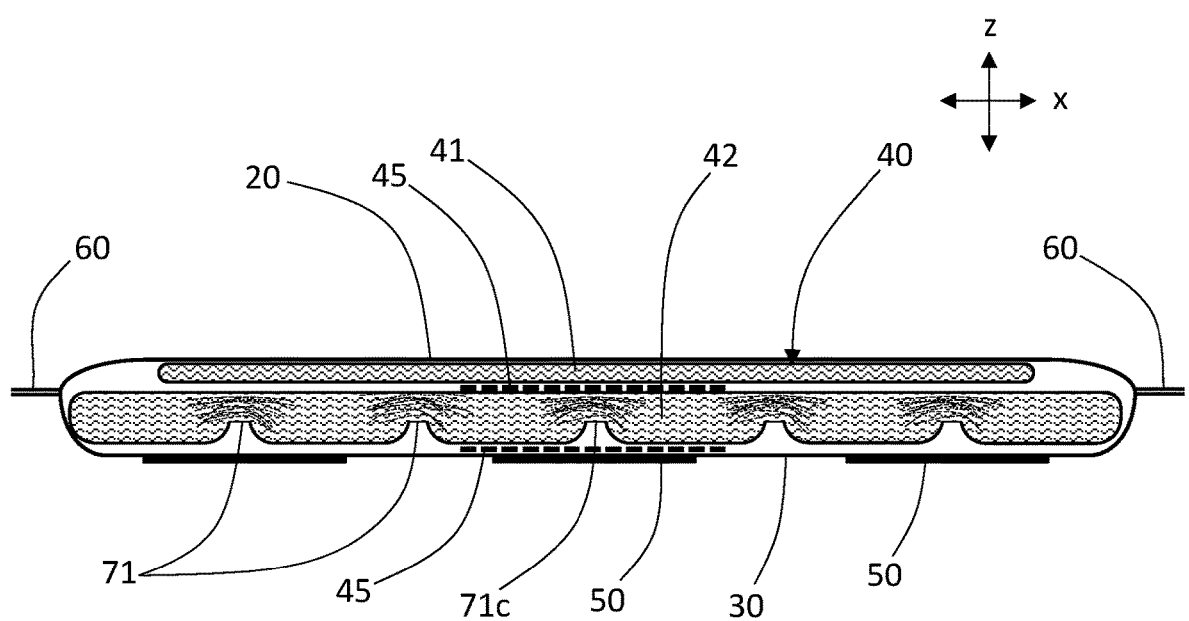
FIG. 4 is a schematic lateral cross section of the feminine hygiene pad shown in FIG. 3, taken along line 4-4 shown in FIG. 3. Details of absorbent structure configuration and components have been omitted for purposes of simplicity and clarity.

Referring to FIGS. 3 and 4, thicker and/or stiffer layers of a feminine hygiene pad 10 (such as an absorbent structure 42) may be imparted with a pattern of compression zones 70, 71, 72. A compression zone for purposes herein is characterized by evidence within an identifiable zone, in which material(s) of the subject component(s) has(have) undergone compression along the z-direction. The compression zones may be zones in which caliper of one or more of the layer components of the pad has been reduced. As a result, the compression zones, appropriately configured, can provide lines or elongate areas that facilitate hinging or flexure, about which the materials of the pad will more easily and readily bend or fold. When the compression zones are appropriately configured, the manner in which the pad gathers laterally may be controlled and improved for better fit against the wearer's body, improved function in use, and improved comfort.

Where the absorbent structure 42 is predominantly or substantially constituted (by weight or by volume) of cellulosic fibers, it may be desired to limit its caliper in the areas that do not include compression zones as described herein. As the caliper of such an absorbent structure increases, the desirable effects of compression zones as described herein are reduced. Accordingly, for an absorbent structure 42 predominantly constituted of cellulosic fibers (by weight or by volume) including compression zones such as, for example, one or more patterns of compression zones 70, 71, 72 as described herein, it may be desired to limit the caliper of such absorbent structure to a maximum of 5 mm. (For purposes herein, any nonwoven web material(s) that wrap and/or separate the absorbent materials of absorbent structure 42 from an overlying STS or topsheet, and/or backsheet, is to be considered part of the absorbent structure 42 and included in the caliper measurement. If loose absorbent materials are disposed directly over the backsheet without any containing nonwoven layer of wrap, the caliper of the backsheet and absorbent structure are to be measured together to determine a combined caliper, and then the caliper of be measured separately, and such backsheet caliper measurement subtracted the combined caliper, to arrive at absorbent structure caliper measurement.)

In some examples, a layer formed of open-celled polyurethane foam may be included, in a position either as an STS 41 or as a layer component of absorbent structure 42. Since polyurethane foam as contemplated herein is a relatively stiff material, and could potentially be the stiffest layer component of a feminine hygiene pad that includes it. In such examples, it may be desired to include compression zones as described herein in such polyurethane foam layer, as an alternative or in addition to including compression zones in other layers of the pad 10.

The compression zones 70, 71 and 72 shown in the figures are depicted as following straight and parallel longitudinal paths. Other configurations may include diagonal paths or curving paths. For purposes herein, the paths defined by the compression zones will preferably be oriented generally longitudinally (i.e., with their larger vector components along the y-direction), but they may be configured to include smaller lateral (x-direction) vector components.

For a layer component including fibers, evidence of z-direction compression may be in the form of fibers that have been plastically deformed, flattened or smashed against each other. For a layer component including particles of AGM (which are typically relatively brittle), such evidence may be in the form of particles that have been fractured. For a layer component including polymer film, such evidence may be in the form of plastic deformation including a reduction of caliper of the film in the compression zone. Such evidence may further include a reduction in caliper in the compression zone of one or more of the layered components of the pad, compared with the caliper of adjacent, uncompressed areas. Evidence of z-direction compression may also include greater material density and consolidation within the compression zones.

While compression zones 70, 71, 72 bear evidence of z-direction compression, generally it is preferred that this not include substantial effects of heating, e.g., melting, fusing, or heat-induced alteration of chemical compositions of components in the compression zones. Heating sufficient to cause melting and fusing of materials may cause bonding therebetween, and thereby impart stiffness to the materials in the compression zones, deemed undesirable for purposes herein. Heating sufficient to cause alteration of chemical compositions (e.g., scorching or burning) can have undesirable effects including increased stiffness, brittleness/frangibility, compromise of beneficial absorbent properties and/or performance, discoloration, etc. For these reasons, the regions overlying or underlying a majority of the x-y surface areas, and preferably substantially all or all of the surface areas, defined by the compression zones, will be devoid of evidence of melting, thermal fusing, or heat-induced alteration of chemical composition of the pad components.

Figure 10:
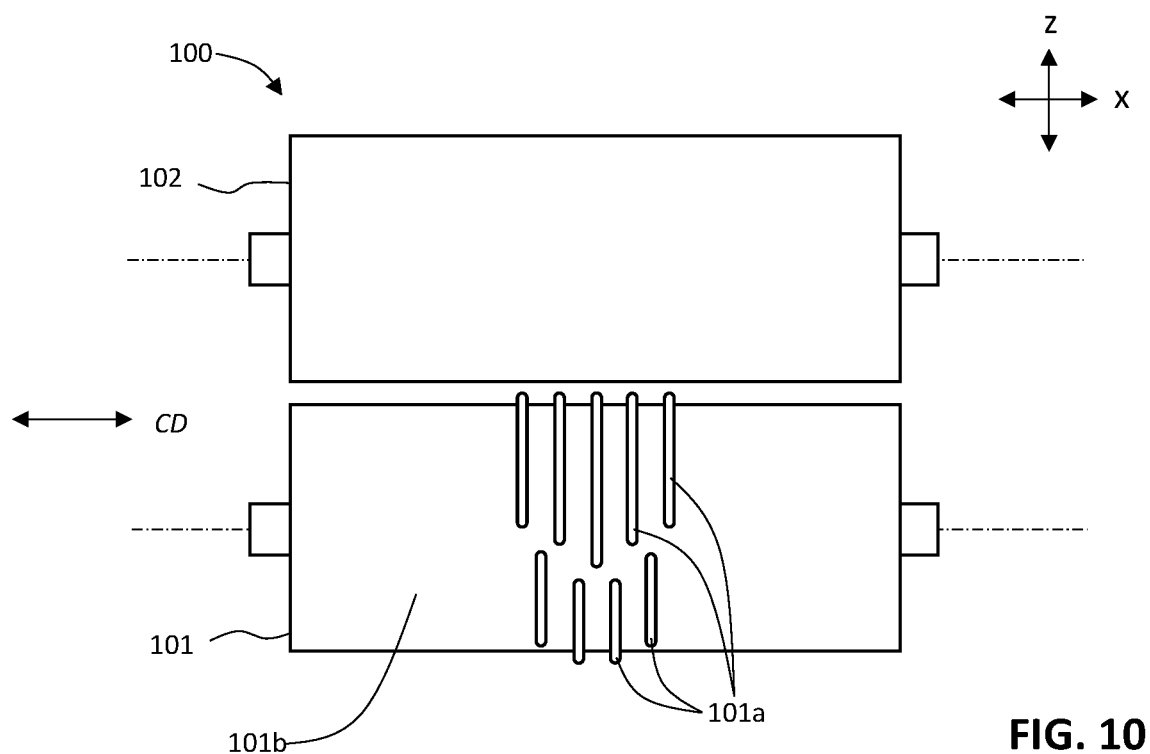
FIG. 10 is a schematic view along the machine direction, of a pair of compressing rollers.

Generally, the compression zones may be created by passing one or more, or any combination, of the layer components of pad 10 through the nip between an appropriately configured pair of rollers, one or both of which has circumferential features such as ridge structures formed thereon, configured to impart the desired pattern of compression zones. For example, referring to FIG. 10, a pair of compressing rollers 101 may include a ridged roller 101 and a cylindrical anvil roller 102. The ridged roller 101 may have formed thereon a group of compressing ridges 101a that extend radially outward beyond the diameter of a cylindrical base surface 101b. The compressing ridges 101a may be configured to impart the desired shapes, lengths and arrangement of compression zones, for example, the arrangement of compression zones 70, 71, 72 depicted in FIG. 3.

It may be preferred that at least the layer component of the pad 10 having the highest uncompressed z-direction caliper be imparted with compression zones; in some examples this will be absorbent structure 42. In combination or alternatively it may be preferred that at least the layer component of the pad 10 having the highest uncompressed z-direction bending stiffness prior to any compression be imparted with compression zones; in some examples this may also be absorbent structure 42. At least the absorbent structure (e.g., absorbent structure 42 as schematically depicted in FIG. 2) may be imparted with such compression zones. In some examples it may be preferred that only the absorbent structure 42 be imparted with compression zones, or alternatively that compression zones are imparted to the absorbent structure 42, but not to the topsheet 20 and/or secondary topsheet 41, and backsheet 30. See, e.g., FIG. 4, schematically depicting a cross section of a pad in which absorbent structure 42 has been imparted with compression zones 71, but the topsheet 20, secondary topsheet 41 and backsheet 30 have not. This preference may be for purposes of avoiding the potential for undesired effects upon, e.g., the topsheet 20 and/or secondary topsheet 41, and backsheet 30—because, for example, these components may include plastically deformable polymer constituents whose plastic deformation from compression may compromise structural integrity, fluid absorbency or wicking performance.

Alternatively, greater hinging/flexure capability may be imparted to the pad by including the STS 41 (if included) in the compression process, along with the absorbent structure 42. The entirety of the absorbent core 40 may be processed so as to be imparted with compression zones if desired. In some examples, it may be desired that all of the layer components of pad 10 above the backsheet, in some examples including the topsheet 20 (in other examples, not including the topsheet 20), include compression zones. The backsheet may be included in some examples, but it may also be desired that it not be included, to avoid the possibility for creating holes through the backsheet in the compression process. The selection of which layer components are imparted with compression zones may depend upon considerations of manufacturing process efficiency, and efficacy of compressing particular layer(s) or combinations of layers to achieve the desired effects described herein. For example, the desired level of hinging/flexure performance may in some pad configurations be achieved without the necessity of including all of the layer components of the pad in the compression process. As suggested in the description above, it is preferable that the compression process not include substantial provision of heating energy, and preferably no provision of heating energy, e.g., to the compressing rollers.

Figure 7A:
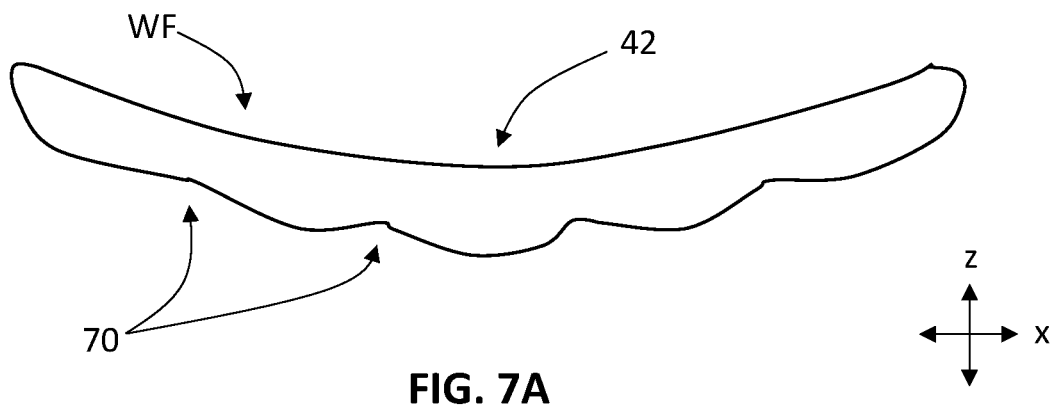
FIG. 7A is a schematic outer profile of a lateral cross section of the absorbent structure component of the feminine hygiene pad as shown in FIG. 6, taken along line 7A-7A shown in FIG. 6. The wearer-facing surface is indicated as "WF".
Figure 7B:
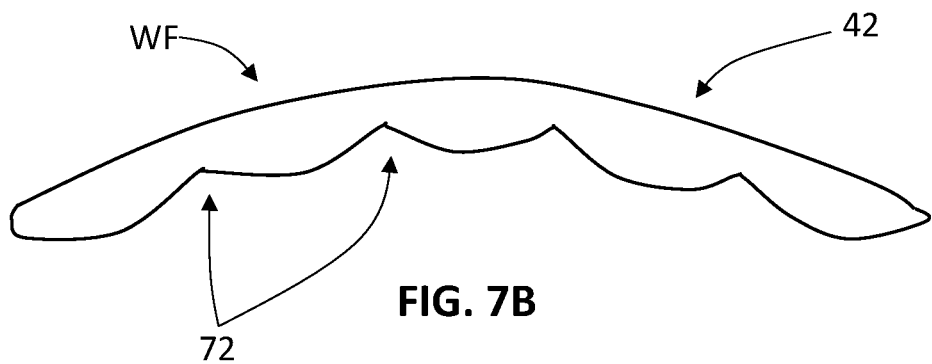
FIG. 7B is a schematic an outer profile of a lateral cross section of the absorbent structure component of the feminine hygiene pad as shown in FIG. 6, taken along line 7B-7B shown in FIG. 6. The wearer-facing surface is indicated as "WF".
Figure 8:
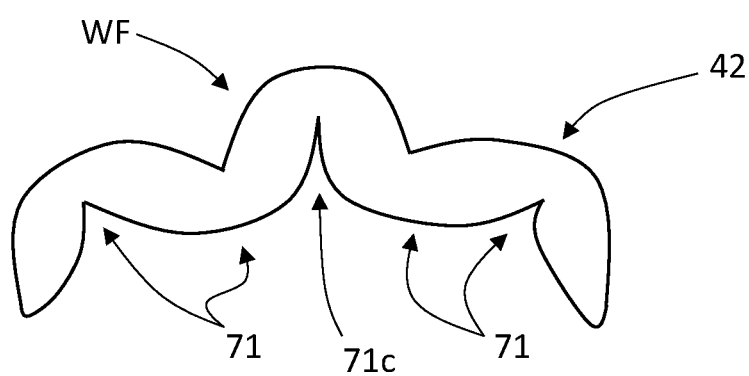
FIG. 8 is a schematic outer profile of a lateral cross section of the absorbent structure component of the feminine hygiene pad as shown in FIG. 6, taken along line 8-8 shown in FIG. 6. The wearer-facing surface is indicated as "WF".

Referring to FIGS. 3, 4, 6, 7A, 7B and 8, through experimentation with prototypes it has been observed that patterns similar to the depicted pattern of forward compression zones 70, middle compression zones 71 and rearward compression zones 72 cause the absorbent structure 42 to assume cross sections with profiles having similarities to those shown in FIGS. 7A, 7B and 8, when the pad 10 is applied to the inside of a pair of underpants in the intended location, and worn. From this work it is believed that the depicted pattern of compression zones 70, 71 and 72 has features that are effective, singly and in combination, at causing pad 10 to gather laterally in a predictable, orderly, effective and comfortable manner in use. As suggested in FIG. 7A, the forward portion of absorbent structure 42, and with it, the pad 10, tend to assume a gentle convex curvature that more closely conforms to wearer's body in the region of the mons pubis. As suggested in FIG. 7B, the rearward portion of the absorbent structure 42, and with it, the pad 10, tend to assume a gentle concave curvature that comfortably straddles the gluteal crevice, but resists complete folding, deeper settling within the gluteal crevice and potential discomfort resulting therefrom, as a result of the arrangement of the respective compression zones 71, 72. As suggested in FIG. 8, the middle portion of the absorbent structure 42, and with it the pad 10, tend to be urged to contract laterally (as suggested by the large arrows in FIG. 6), facilitated by folding in accordion-fashion with a general concave curvature that fits predictably and comfortably between the wearer's legs, and conforms closely to the body in the region of the vaginal opening. This combination of curvatures facilitated by the compression zones 70, 71 and 72 as described herein can impart to a pad the ability to better conform closely to the wearer's body, and be more comfortable to wear, and be more discreet under outer clothing. (In FIGS. 7A, 7B and 8 the wearing-facing surfaces of the absorbent structure 42 are designated as "WF".)

These benefits are believed to result from the following features.

Figure 9:
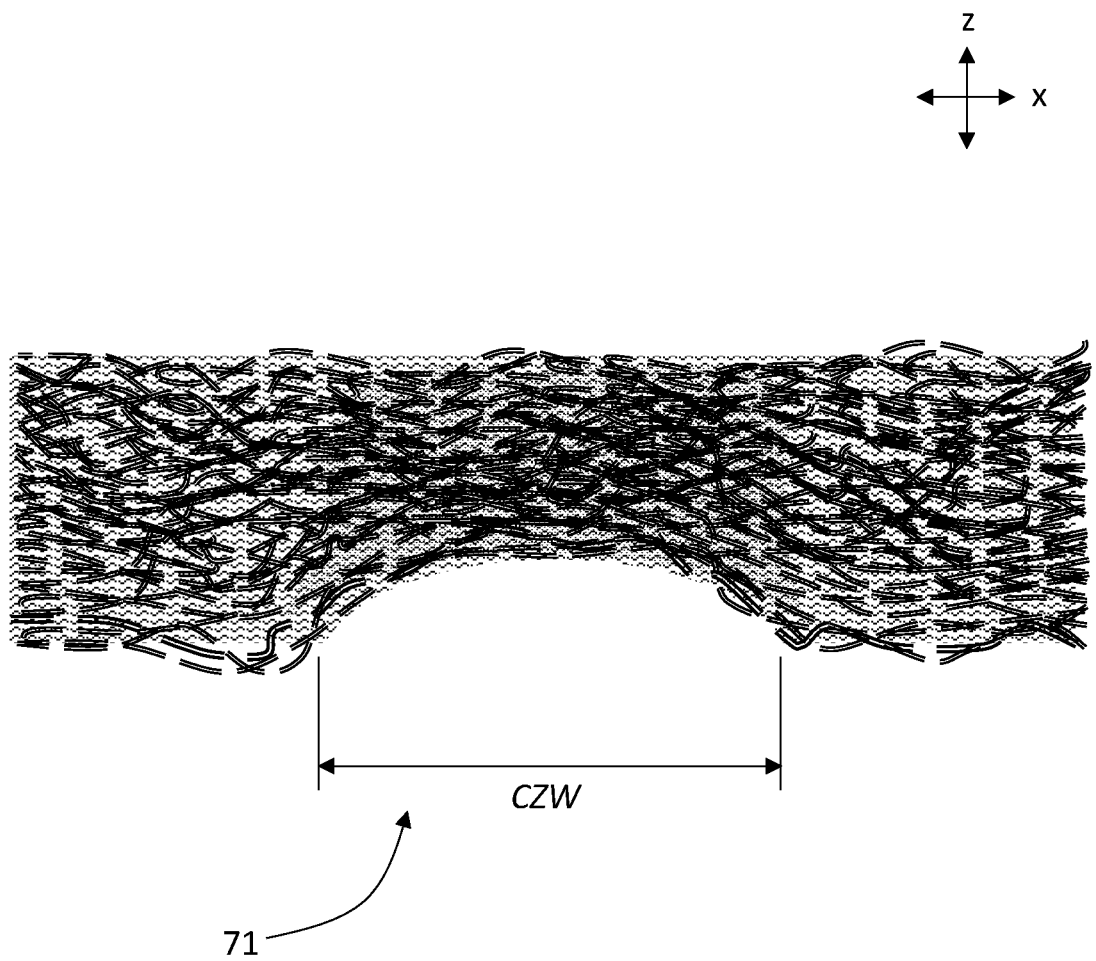
FIG. 9 is an expanded, schematic lateral cross section of an example of an absorbent structure, taken through a compression zone, taken along line 4-4 shown in FIG. 3.

First, the compression zones define relatively narrow pathways. They may be created to have an average lateral width of about 0.5 mm to about 2.0 mm (and including all identifiable sub-ranges therewithin). It is preferred that these widths be relatively small to avoid excessively compromising the wicking and absorption properties of the materials by excessive consolidation, and to promote focused folding therealong. Referring to FIG. 9, width CZW of a compression zone may be measured visually, using any suitable magnification and measurement equipment and technique. The edges of a compression zone defining its width will be demarked by evidence of contact by the tooling (e.g., a compressing roller 101 bearing circumferential compressing ridges 101a), used to create the compression zones 70, 71, 72, upon the surface of the material. Alternatively, width CZW will substantially correlate with the cross direction width of the compressing ridge 101a on the roller 101 that imparted the compression zone. In combination therewith, to enhance the folding/hinging effect, particularly in the longitudinal middle/central region of the pad, the average lateral spacing between any two or more of the compression zones may be configured to be 3 mm up to 10 mm, more preferably 5 mm to 10 mm and even more preferably 5 mm to 8 mm. Such spacing may be desired to promote folding in respectively alternative directions along the width of the pad, in accordion fashion, as suggested in FIG. 8.

Second, as noted above, the compression zones are generally oriented longitudinally, such that they promote longitudinal hinging or flexure, and folding, therealong, so as to facilitate orderly gathering in accordion-like fashion in a lateral direction (along the directions of the large arrows in FIG. 6), and as suggested in FIGS. 7 and 8.

Third, there are an odd number of middle compression zones 71 occupying the middle region 10m of the pad 10, which includes the location of intersection of lateral axis 200 and longitudinal axis 100, including a central compression zone 71c. This feature promotes symmetrical gathering centering about a fold about the central compression zone 71c, as may be appreciated from FIG. 8. Such centered symmetrical gathering is better adapted for close fit against the user/wearer's body in the crotch region. The pad may be imparted with 1, 3, 5 or even 7 middle compression zones 71. Generally, the number of middle compression zones 71 desired may be selected according to the overall z-direction caliper of the pad 10. Fewer middle compression zones 71 may be desired for a relatively thick (higher z-direction caliper) pad, while more may be desired for a relatively thin (lower z-direction caliper) pad. Additionally, the number of middle compression zones 71 desired may be selected according to the total width of the pad 10 in the middle region 10m; a greater number of middle compression zones 71 may be desired for a wider pad, while a lesser number of middle compression zones 71 may be desired for a narrower pad.

Fourth, the middle compression zones 71 do not extend along the entire length of the pad 10. Rather, even the longest of the middle compression zones 71 stops short of one or both the forward and rearward ends 11, 12 of the pad 10. This is because lateral gathering and accordion-like longitudinal folding to the same extent as may be desired in the middle region 10m of the pad may not be required or desired in the forward and rearward end regions 10f, 10r of the pad.

Rather, it may be desired that the forward and/or rearward end regions of the pad assume a relatively more flat or only slightly folded or arched (concave/convex) lateral cross section configuration during wear. For example, it may be desired that the pad assume a gentle convex curvature against the wearer's body in the forward region (forward of the vaginal opening, in the region of the mons pubis) to better conform to the wearer's body and thereby be both more discreet under clothing, and be better positioned to intercept any fluid that may move forwardly along skin surfaces. It also be desired that the pad laterally gather only slightly to the rear of the vaginal opening, to avoid having a substantially gathered pad disposed in the gluteal crevice, potentially creating a source of discomfort. Depending upon the overall length of the pad 10, it may be desired that one or more of middle compression zones 71, 71c extend to respective forward and rearward termini that lie no more than 30 percent of the total length of the pad 10 forward and rearward of the lateral axis 200 of the pad 10 (and having a longitudinal dimension no greater than 60 percent of the total length of the pad), leaving forward and rearward regions of the pad unoccupied by the same compression zones 71, 71c. At the same time, for the middle compression zones to have the desired effects described herein, it may be desired that one or more of middle compression zones 71, 71c extend at least 16.7 percent of the total length of the pad forward and rearward of the lateral axis 200 of the pad 10 (and having a longitudinal dimension no less than 33 percent of the total length of the pad).

In combination with the feature described immediately above, it may be desired that there are intermediate regions forward and/or rearward of the middle compression zones 71, 71c, into which middle compression zones 71, 71c do not longitudinally extend. These serve as fold interruption margins 73, traversing/extending laterally across the pad. This may be desired for the purpose of preventing folds along middle compression zones 71, 71c from propagating along the length of the pad 10 toward the forward and/or rearward ends 11, 12 of the pad. Fold interruption margins 73, into which one or more of middle compression zones 71, 71c do not longitudinally extend, may be present at locations that are 16.7 percent to 30 percent of the length of the pad 10 forward and/or rearward of the lateral axis 200 of the pad.

In some examples, fold interruption margins 73 may be characterized by a region of y-direction separation between terminal ends of the middle compression zones 71 and proximate terminal ends of the forward and/or rearward compression zones 70, 72, with no compression zones therebetween. Alternatively characterized, referring to FIG. 3, for example, each of the rearward termini 70tr of forward compression zones 70 lies longitudinally short of the forward termini 71tf of the nearest of the middle compression zones 71, 71c, along the longitudinal direction of the pad, as illustrated. A similar arrangement is present toward/at the rearward end region 10r of the pad. As suggested by the example shown in FIG. 3, the margins may have a "V" or other nonlinear laterally extending configuration defined by forward 73f and rearward 73r boundaries; but the margins also may be linear, i.e., have forward and/or rearward boundaries 73f, 73r that are straight and oriented along the x-direction, or have other shapes or profiles.

Sixth, it may be desired to include additional forward compression zones 70 and/or rearward compression zones 72, proximate the forward and/or rearward ends 11,12 of the pad, respectively. These may be included to relieve stresses in the forward and rearward end regions of the layer(s) bearing middle compression zones 71, 71c, resulting from folds along the middle compression zones 71, 71c and gathering in the middle region 10m of the pad, that may otherwise cause the forward and/or rearward end regions to buckle in uncontrolled fashion, creating the potential for wearer discomfort and/or an irregular bulky/non-discreet appearance under outer clothing. As suggested in the figures, forward compression zones 70 and/or rearward compression zones 72 may be laterally offset from the middle compression zones 71, 71c. They may be arranged substantially symmetrically about longitudinal axis 100, and may be even in number, for example, 2, 4 or 6. As with the middle compression zones 71, 71c, selection of the number of forward and/or rearward compression zones 70, 72 included may be affected by the overall z-direction caliper of the layer on which they are imparted, e.g., absorbent structure 42. Fewer compression zones in the end regions 10f, 10r may be desired for a relatively thick (higher z-direction caliper) pad, while more may be desired for a relatively thin (lower z-direction caliper) pad. Generally, it may be desired that the number of either forward or rearward compression zones 70, 72 included be fewer in number than the number of middle compression zones 71, 71c included, to help effect a more flattened configuration for the pad 10 in the end region(s) during use/wear. In some examples, as suggested in FIG. 3, an even number of forward and/or rearward compression zones 70, 72 may be one less than an odd number of middle compression zones 71, 71c.

Like the middle compression zones 71, 71c, forward and/or rearward compression zones 70, 72 may serve to promote hinging/flexing and folding of the pad therealong, but their lateral positions, being offset from those of the middle compression zones 71, 71c further help prevent folds through the middle compression zones 71, 71c from propagating to the forward and rearward ends of the pad 10. As result of the break and change in the folding pattern created by fold interruption margins 73 and laterally offset placement of forward and rearward compression zones 70, 72, the forward and rearward end regions of the pad may be caused to bend or fold less dramatically, but in a controlled fashion, and thereby assume a relatively more flat (more gently curved) configuration in the end regions as compared with the middle region—as suggested in a comparison between FIGS. 7A and 7B (cross section through forward and rearward end regions), and FIG. 8 (cross section through middle region).

Figure 5A:
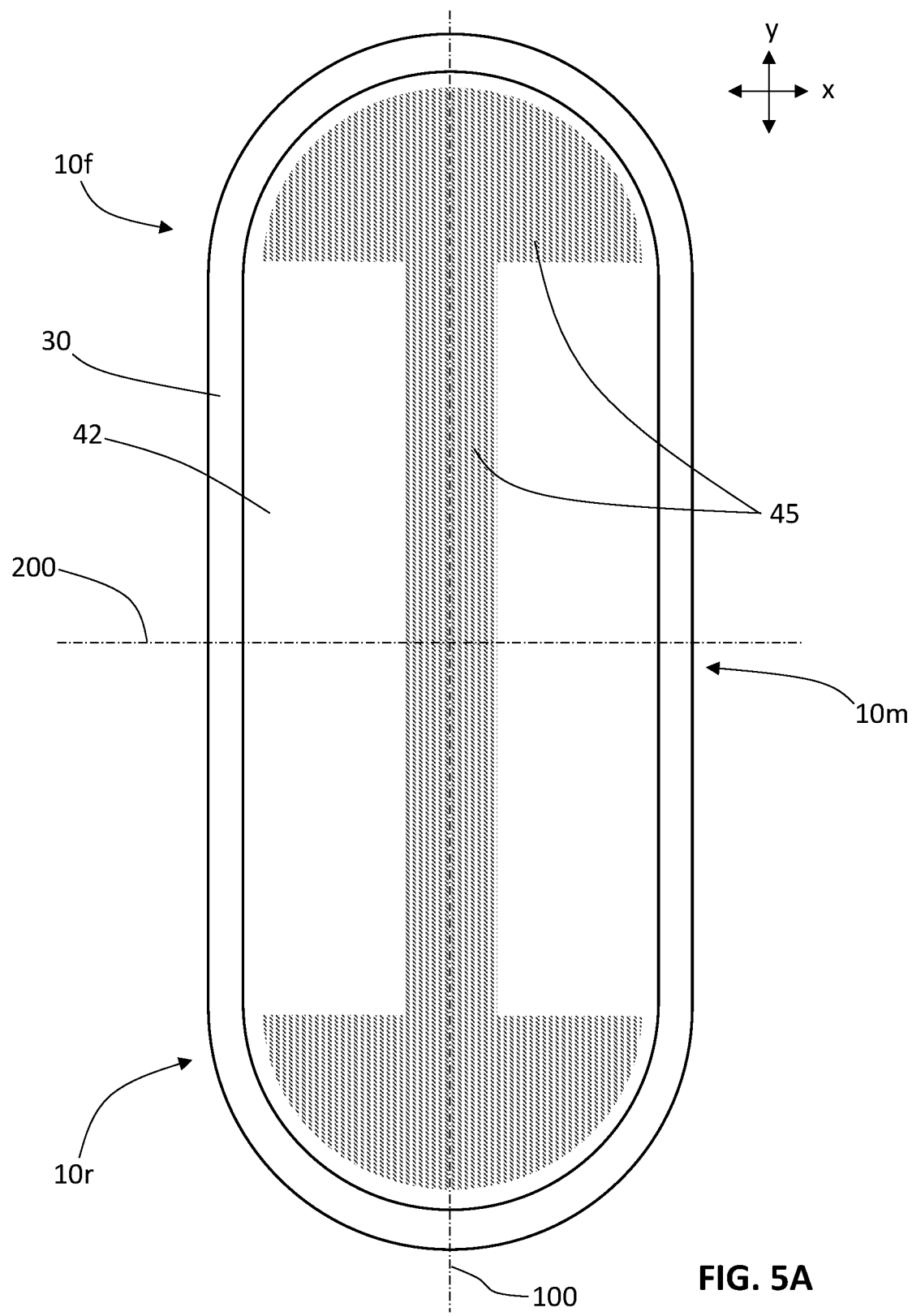
FIG. 5A is a schematic plan view of an example of a particular layer component of a feminine hygiene pad overlying a backsheet, bearing a configuration of an application of adhesive.
Figure 5B:
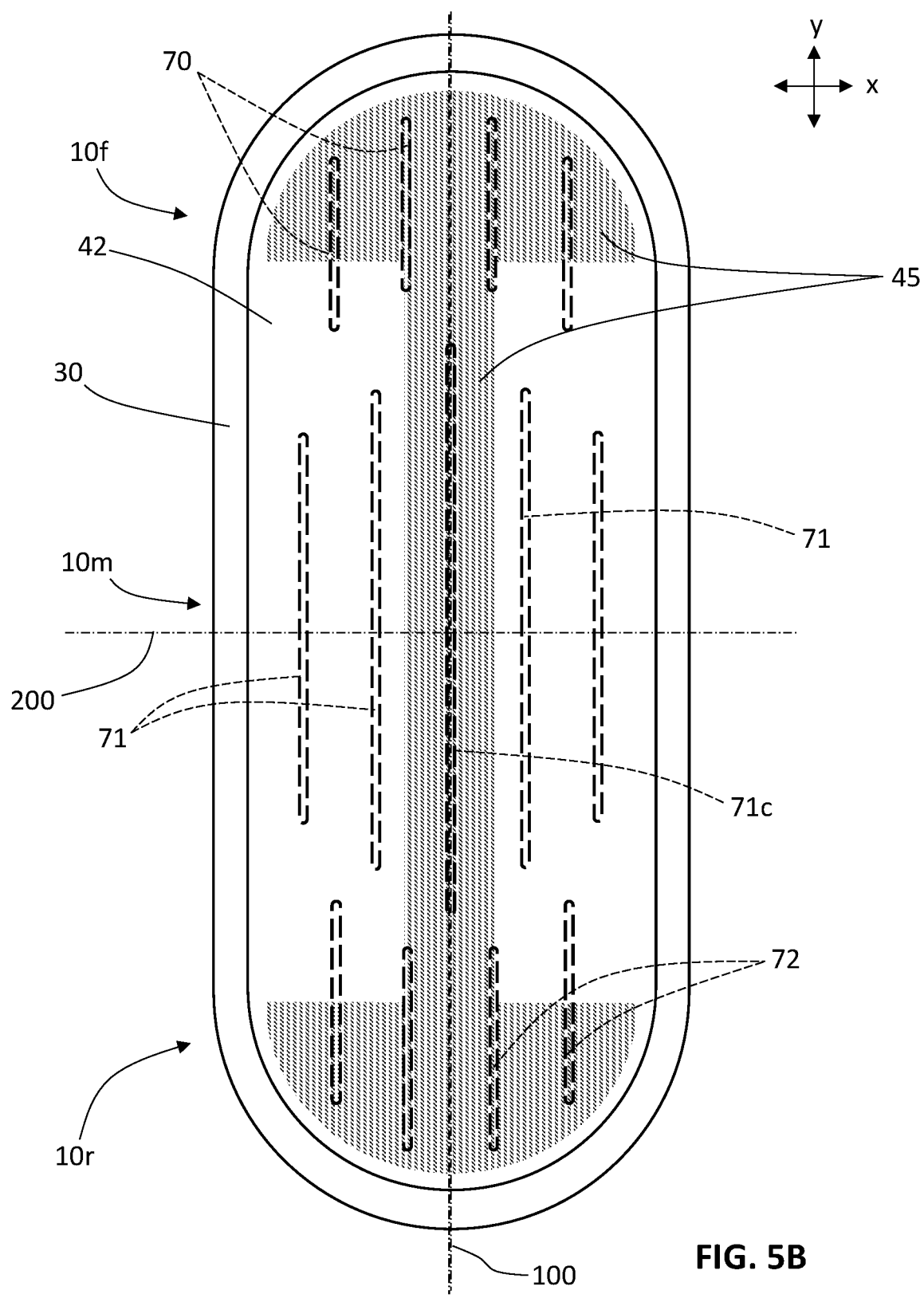
FIG. 5B is a schematic plan view of an example of a particular layer component of a feminine hygiene pad overlying a backsheet, bearing a configuration of an application of adhesive, and showing an example of dimension and location relationships thereof with respect to dimensions and locations of compression zones.
Figure 6:
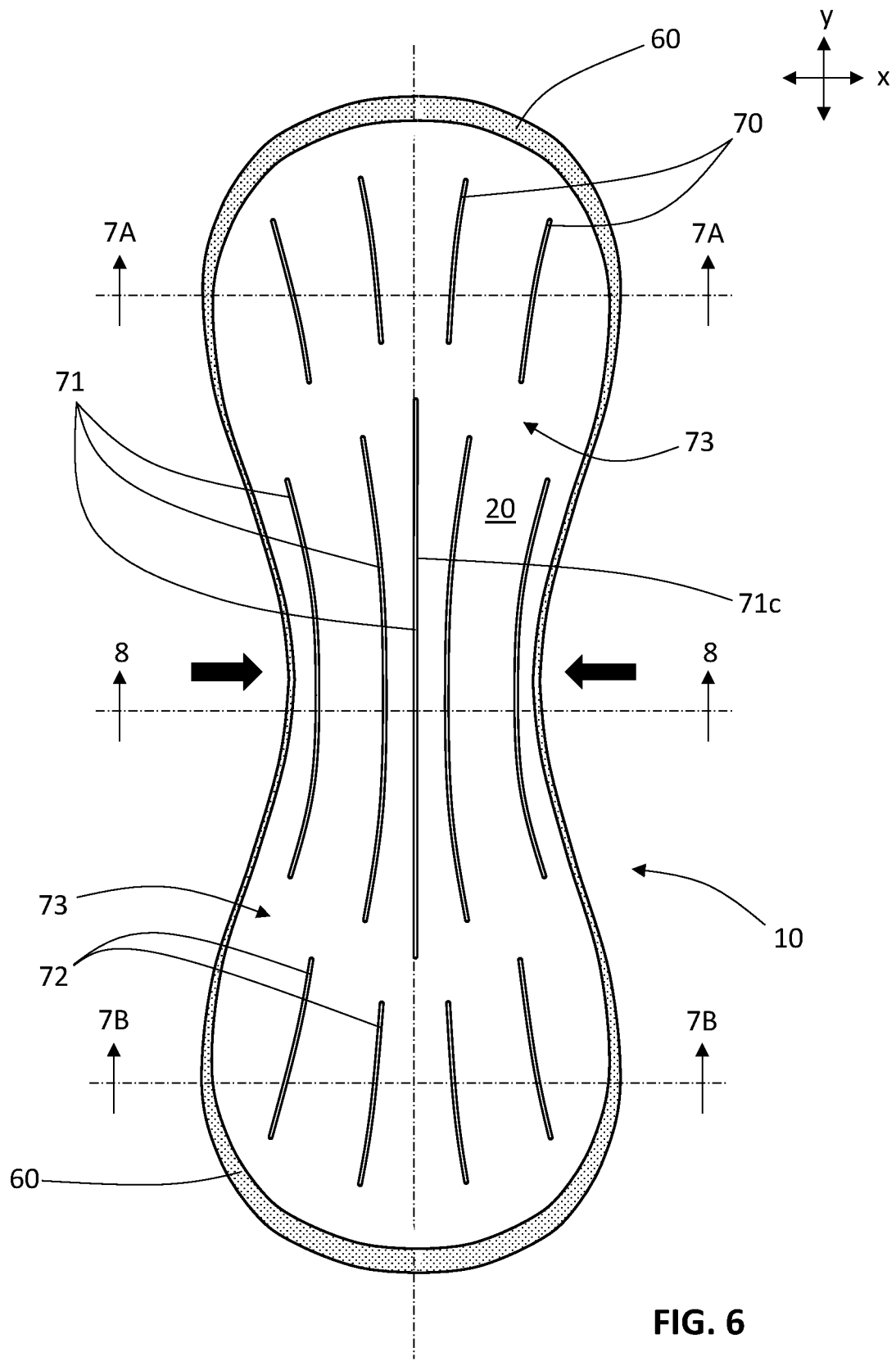
FIG. 6 is a schematic plan view of the example of a feminine hygiene pad as shown in FIG. 3, shown in a laterally gathered configuration.

The pad 10 may include one or more internal deposits of core adhesive 45, adhering the absorbent structure 42 to superadjacent and/or subjacent layers. This is to help unify the structure. Referring to FIGS. 4, 5A and 5B, in combination with the features described above, the deposits of core adhesive 45 may be varied in relative quantity and/or coverage area of deposited adhesive, between the middle region 10m and one or both the end regions 10f. 10r. In the example illustrated in the figures, deposits of adhesive 45 are positioned to adhere absorbent structure 42 to a subjacent backsheet 30 and/or superadjacent STS 41. As suggested in FIGS. 5A and 5B, the core adhesive 45 may be deposited in a pattern or configuration such that it has a laterally narrower profile in the middle region 10m of the pad, than in one or both of the end regions 10f, 10r. Alternatively, the adhesive may be deposited to a lesser basis weight, such as in a more sparse or widely distributed pattern of application, in the middle region 10m as compared with one or both of the end regions 10f, 10r. Application of adhesive between component layers of a pad will add z-direction bending stiffness to the structure. Accordingly, the purpose of varying the distribution of core adhesive 45 as described above is to better retain flexibility of the assembly, for purposes of permitting folding along the middle compression zones 71 and lateral gathering. At the same time, a greater basis weight fraction and/or laterally wider distribution of core adhesive deposit 45 in one or both of the end regions 10f, 10r will impart added z-direction bending resistance to those regions, which may be deemed not deleterious, or even advantageous, for purposes of greater stiffness that helps limit gathering of the end regions to a more gently curved (i.e., flatter) configuration as compared with the middle region, in a manner suggested in FIGS. 7A and 7B. In some examples it may be preferred that the lateral middle of the pad (the area including the longitudinal axis 100) be occupied by deposit(s) of core adhesive 45, through the longitudinal middle marked by the lateral axis 200, as suggested in FIG. 5. This will impart bending stiffness to the middle region, that will resist bending and folding along a generally centrally located compression zone such as central compression zone 71c (see FIGS. 6 and 8) to some extent, thereby tending to prevent the structure from forming a sharp longitudinal fold in the middle region, that may create a source of discomfort for the wearer. As suggested in FIG. 5B, in some examples the central deposit of core adhesive 45 may have a width along the lateral axis such that it is disposed over an area superadjacent and/or subjacent only central compression zone 71c, but not middle compression zones 71 immediately laterally outlying central compression zone 71c to either side thereof. In other examples the central deposit of core adhesive 45 may have a width along the lateral axis such that it is disposed over an area superadjacent and/or subjacent central compression zone 71c as well as middle compression zones 71 immediately laterally outlying central compression zone 71c to either side thereof. The choice of such width of adhesive deposit 45 along the lateral axis 200 may depend upon the number and lateral spacing of middle compression zones included, and the degree of added bending stiffness needed to prevent the pad from assuming an uncomfortably sharply longitudinally folded configuration. [For purposes of this description of core adhesive deposit(s) 45, the middle region 10m of the pad is the region making up the middle one-third of the total length of the pad.]

Caliper Measurement Method

The Caliper of a sample of a layer component of a feminine hygiene pad is measured as the distance between a reference platform on which the sample rests and a pressure foot that exerts a specified amount of pressure onto the sample over a specified amount of time. All measurements are performed in a laboratory maintained at 23° C.±2 C.° and 50%+2% relative humidity.

Caliper is measured with a manually-operated micrometer equipped with a pressure foot capable of exerting a steady pressure of 0.5 kPa±0.01 kPa onto the test sample. The manually-operated micrometer is a dead-weight type instrument with readings accurate to 0.001 mm. A suitable instrument is Mitutoyo Series 543 ID-C Digimatic, available from VWR International, or equivalent. The pressure foot is a flat ground circular movable face with a diameter of 30 mm. The sample is supported by a horizontal flat reference platform that is larger than and parallel to the surface of the pressure foot. The system is calibrated and operated per the manufacturer's instructions.

Obtain a square sample of the layer of interest 30 mm by 30 mm (with sides parallel and perpendicular, respectively, to the longitudinal axis of the pad, measured in x-y directions) centered at the intersection of the longitudinal and lateral axes of the pad, by excising it therefrom, nondestructively separating layers to the extent necessary, to separate out the layer of interest. A freeze spray may be used to deactivate any adhesives present, to facilitate separation. (Alternatively, an assembly of materials such as, for an absorbent structure, an assembly of a nonwoven web material and affixed or embedded AGM particles, constituting the layer of interest, may be measured prior to incorporation into a finished pad product.) Samples are to be conditioned at 23° C.±2 C.° and 50%±2% relative humidity for 2 hours prior to measurement. To measure caliper, first zero the micrometer against the horizontal flat reference platform. Place the sample on the platform, centered beneath the pressure foot. Gently lower the pressure foot with a descent rate of 1.0 mm+0.1 mm per second until the full pressure specified above is exerted on the sample. Wait 5 seconds and then record the caliper of the sample to the nearest 0.01 mm. In like fashion, repeat for a total of 10 replicate samples. Calculate the arithmetic mean for the Caliper and report to the nearest 0.01 mm. (If the feminine hygiene pad of interest is not wide enough to yield a sample of a layer thereof that is at least 30 mm wide at the specified location, then the pad is deemed to be outside of the scope of any claims herein that recite a caliper element.)

In view of the foregoing description, the following non-limiting examples are contemplated:

1. A feminine hygiene pad having a length, and comprising a topsheet, a backsheet, an absorbent core disposed between the topsheet and the backsheet, a forward end region, a rearward end region, a middle region, a longitudinal axis and a lateral axis, the absorbent core comprising:
   an absorbent structure having:
      a first plurality of central compression zones disposed in the middle region, each of the first plurality of compression zones being defined by a generally longitudinally-oriented shape having a forward terminus proximate the forward end region and a rearward terminus proximate the rearward end region, and an average width between the forward terminus and rearward terminus of 0.5 mm to 2.0 mm, wherein each of the forward terminus and rearward terminus lies no more than 30 percent of the length, from the lateral axis.
2. The feminine hygiene pad of example 1 wherein the absorbent structure is predominantly constituted of cellulosic fibers by weight and/or by volume.
3. The feminine hygiene pad of either of examples 1 or 2 wherein the first plurality is an odd number and is substantially laterally centered about the longitudinal axis.
4. The feminine hygiene pad of any of the preceding examples wherein the compression zones of the first plurality have dimensions along a longitudinal direction that vary.
5. The feminine hygiene pad of any of the preceding examples wherein the dimension along a longitudinal direction of a laterally outwardly-disposed compression zone is less than that of a laterally more inwardly-disposed compression zone.
6. The feminine hygiene pad of any of the preceding examples comprising one or two second pluralities of end region compression zones disposed in either or both of the forward end region and rearward end region, each of the plurality of end compression zones being defined by a generally longitudinally-oriented shape having an endward terminus proximate an end of the pad and an inward terminus proximate the middle region, and an average width between the end terminus and inward terminus of 0.5 mm to 2.0 mm.
7. The feminine hygiene pad of example 6 wherein each of the inward termini of the end compression zones of one or both of the second pluralities lies longitudinally short of any of the nearest termini of the middle compression zones.
8. The feminine hygiene pad of either of examples 6 or 7 wherein one or both of the second pluralities is an even number and is substantially centered about the longitudinal axis.
9. The feminine hygiene pad of any of examples 6-8 wherein one or both of the second pluralities is lower in number than the first plurality.
10. The feminine hygiene pad of any of examples 6-9 wherein a fold interruption margin is disposed between the one or both of the second pluralities and the first plurality.
11. The feminine hygiene pad of any of the preceding examples wherein the absorbent structure is adhered to one or both a subjacent layer and a superadjacent layer by a deposit of adhesive defining an adhesive shape along an x-y plane.
12. The feminine hygiene pad of example 11 wherein the deposit of adhesive is applied in a lesser quantity per unit x-y surface area in the middle region, than in one or both of the forward and rearward end regions.
13. The feminine hygiene pad of examples 11 or 12 wherein the adhesive shape has a width that varies along the length of the absorbent structure.
14. The feminine hygiene pad of example 13 wherein the adhesive shape has a lesser width proximate the middle region, and a greater width proximate one or both the forward end region and rearward end region
15. The feminine hygiene pad of any of examples 11-14 wherein the subjacent layer is the backsheet.
16. The feminine hygiene pad of any of examples 11-15 wherein the superadjacent layer is a secondary topsheet or acquisition layer.
17. The feminine hygiene pad of any of the preceding examples wherein the absorbent structure comprises a distribution of AGM particles.
18. The feminine hygiene pad of any of the preceding examples wherein the absorbent structure has a caliper no greater than 5.0 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A feminine hygiene pad having a length, and comprising a topsheet, a backsheet, an absorbent core disposed between the topsheet and the backsheet, a forward end region, a rearward end region, a middle region, a longitudinal axis and a lateral axis, the absorbent core comprising:
    an absorbent structure having:
        a first plurality of compression zones disposed in the middle region, each of the first plurality of compression zones being defined by a generally longitudinally-oriented shape having a forward terminus proximate the forward end region and a rearward terminus proximate the rearward end region, and an average width between the forward terminus and rearward terminus of 0.5 mm to 2.0 mm, wherein at least two of the first plurality of compression zones have a longitudinal dimensions along a longitudinal direction that vary, wherein each of the first plurality of compression zones extend across a lateral axis of the absorbent structure, wherein one of the first plurality of compression zones extends substantially along the longitudinal axis, wherein each of the first plurality of compression zones extends from a first surface of the absorbent core adjacent to the backsheet toward a second surface of the absorbent core adjacent to the topsheet, and wherein the absorbent structure is compressed in the first plurality of compression zones.

2. The feminine hygiene pad of claim 1 wherein the absorbent structure is predominantly constituted of cellulosic fibers by weight and/or by volume.

3. The feminine hygiene pad of claim 1 wherein the first plurality is an odd number and is substantially laterally centered about the longitudinal axis.

4. The feminine hygiene pad of claim 1 wherein the compression zones of the first plurality have dimensions along the longitudinal direction that vary.

5. The feminine hygiene pad of claim 1 wherein the dimension along a longitudinal direction of a laterally outwardly-disposed compression zone is less than that of a laterally more inwardly-disposed compression zone.

6. The feminine hygiene pad of claim 1 comprising one or two second pluralities of end region compression zones disposed in either or both of the forward end region and rearward end region, each of the plurality of end compression zones being defined by a generally longitudinally-oriented shape having an endward terminus proximate an end of the pad and an inward terminus proximate the middle region, and an average width between the end terminus and inward terminus of 0.5 mm to 2.0 mm.

7. The feminine hygiene pad of claim 6 wherein each of the inward termini of the end compression zones of one or both of the second pluralities lies longitudinally short of any of the nearest termini of the middle compression zones.

8. The feminine hygiene pad of either of claim 6 wherein one or both of the second pluralities is an even number and is substantially centered about the longitudinal axis.

9. The feminine hygiene pad of claim 6 wherein one or both of the second pluralities is lower in number than the first plurality.

10. The feminine hygiene pad of any of claim 6 wherein a fold interruption margin is disposed between the one or both of the second pluralities and the first plurality.

11. The feminine hygiene pad of claim 1 wherein the absorbent structure is adhered to one or both a subjacent layer and a superadjacent layer by a deposit of adhesive defining an adhesive shape along an x-y plane.

12. The feminine hygiene pad of claim 11 wherein the deposit of adhesive is applied in a lesser quantity per unit x-y surface area in the middle region, than in one or both of the forward and rearward end regions.

13. The feminine hygiene pad of claim 11 wherein the adhesive shape has a width that varies along the length of the absorbent structure.

14. The feminine hygiene pad of claim 13 wherein the adhesive shape has a lesser width proximate the middle region, and a greater width proximate one or both the forward end region and rearward end region.

15. The feminine hygiene pad of claim 11 wherein the subjacent layer is the backsheet.

16. The feminine hygiene pad of any of claims 11-15 wherein the superadjacent layer is a secondary topsheet or acquisition layer.

17. The feminine hygiene pad of claim 1 wherein the absorbent structure comprises a distribution of AGM particles.

18. The feminine hygiene pad of claim 1 wherein the absorbent structure has a caliper no greater than 5.0 mm.

19. A feminine hygiene pad having a length, and comprising a topsheet, a backsheet, an absorbent core disposed between the topsheet and the backsheet, a forward end region, a rearward end region, a middle region, a longitudinal axis and a lateral axis, the absorbent core comprising:
    an absorbent structure comprising a first plurality of compression zones and a second plurality of compression zones, wherein the absorbent structure in each of the first plurality of compression zones and the second plurality of compression zones is compressed,
    wherein the first plurality of compression zones disposed in the middle region, each of the first plurality of compression zones being defined by a generally longitudinally-oriented shape having a forward terminus proximate the forward end region and a rearward terminus proximate the rearward end region, wherein each of the first plurality of compression zones extend across a lateral axis of the absorbent structure, and wherein one of the first plurality of compression zones extends substantially along the longitudinal axis;
    wherein the second plurality of compression zones disposed in the reward end region or the forward end region, each of the second plurality of compression zones being defined by a generally longitudinally-oriented shape having a forward terminus proximate the forward end region and a rearward terminus proximate the rearward end region,
    wherein the second plurality of compression zones is less than the first plurality of compression zones.

20. The feminine hygiene pad of claim 19 comprising a fold interruption margin between the first plurality of compression zones and the second plurality of compression zones, wherein the fold interruption margin extends laterally in a nonlinear configuration.

* * * * *